United States Patent [19]

Danks et al.

[11] Patent Number: 5,607,440
[45] Date of Patent: Mar. 4, 1997

[54] TROCAR WITH LOCKABLE SHIELD

[75] Inventors: John K. Danks, Boca Raton, Fla.;
Richard V. Mazzola, Bloomfield, N.J.;
Thomas R. Johnson, Milford, N.H.

[73] Assignee: Endoscopic Concepts, Inc., Delray Beach, Fla.

[21] Appl. No.: 459,331

[22] Filed: Jun. 2, 1995

Related U.S. Application Data

[62] Division of Ser. No. 238,959, May 6, 1994, Pat. No. 5,545,150.

[51] Int. Cl.[6] ........................................ A61B 17/34
[52] U.S. Cl. ........................ 606/185; 604/265; 604/264
[58] Field of Search ................................ 604/164, 171, 604/264, 165; 606/184, 185, 167

[56] References Cited

U.S. PATENT DOCUMENTS

| | | | |
|---|---|---|---|
| 4,535,773 | 8/1985 | Yoon | 606/185 |
| 5,112,308 | 5/1992 | Olsen | 604/164 |
| 5,275,583 | 1/1994 | Crainich | 604/164 |
| 5,411,515 | 5/1995 | Haber et al. | 604/164 |

FOREIGN PATENT DOCUMENTS

| | | | |
|---|---|---|---|
| 2697150 | 4/1994 | France | 606/185 |

*Primary Examiner*—Glenn Dawson
*Attorney, Agent, or Firm*—Miller & Martin

[57] ABSTRACT

A trocar is formed from a cannula and an interfitting obturator for penetrating body cavity walls in laparoscopic and endoscopic surgery. The obturator is provided with an improved piercing tip having a pointed blade and an improved double locking blunt nosed shield design. Hydrophilic coatings or components are also employed on the shield and cannula to facilitate quicker shield action covering the pointed blade and ease of entry of the cannula tube through the body cavity wall. The cannula also has an improved inexpensive flexible flapper valve and can be manufactured with a reusable cannula tube but disposable flapper valve assembly to minimize cost. The shield locks in a partially retracted position whereby the point of the blade is covered, but sharp lateral portions are exposed.

20 Claims, 5 Drawing Sheets

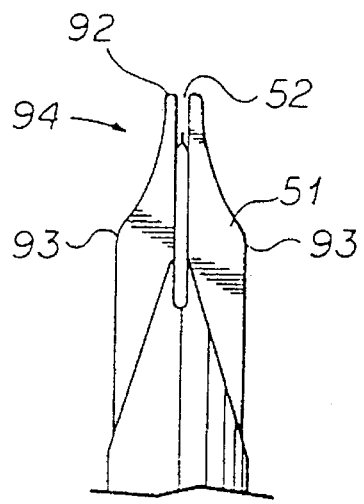
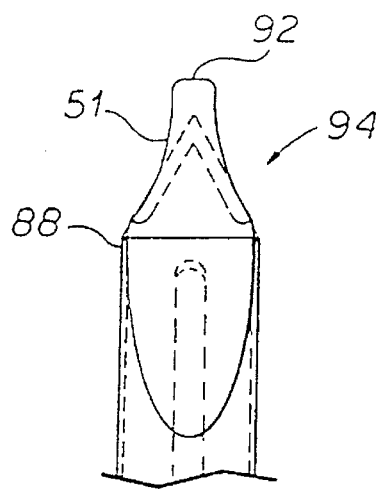
FIG 7A  FIG 7B
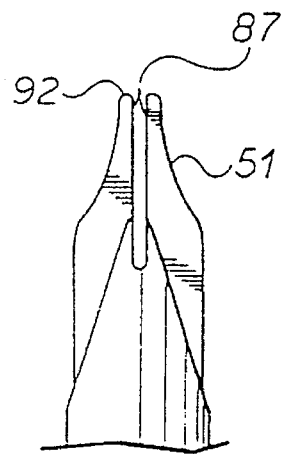
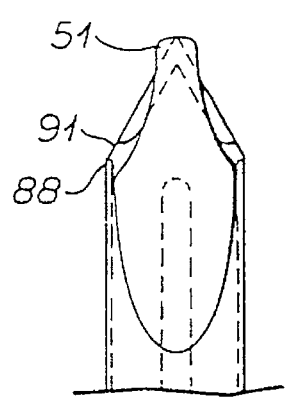
FIG 8A  FIG 8B
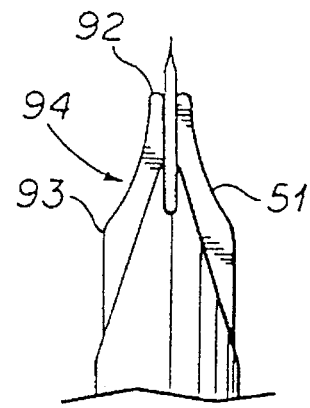
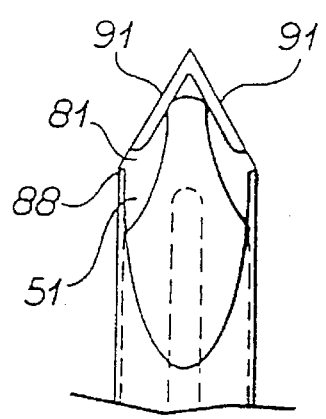
FIG 9A  FIG 9B

TROCAR WITH LOCKABLE SHIELD

This application is a division of application Ser. No. 08/238,959, filed May 6, 1994, now U.S. Pat. No. 5,545,150.

BACKGROUND OF THE INVENTION

The present invention relates to a surgical instrument commonly referred to as a trocar, or an obturator and cannula, often used in laparoscopic or arthroscopic surgery. More particularly, the invention relates to new and improved designs for shields, seals, and coatings, and to the use of disposable seal and stopcock assemblies on an otherwise reusable instrument.

Many surgical procedures are now being performed with the use of trocars and cannulas. Originally these devices were used for making a puncture and leaving a tube to drain fluids. As technology and surgical techniques have advanced, it is now possible to insert surgical instruments through the cannulas and perform invasive procedures through openings less than half an inch in diameter. Previously these procedures required incisions of many inches. By minimizing the incision, the stress and loss of blood suffered by patients is reduced and the patients' recovery times are dramatically reduced.

Surgical trocars are most commonly used in laparoscopic surgery. Prior to use of the trocar, the surgeon will usually introduce a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, pneumoperitoneum is created separating the wall of the body cavity from the internal organs.

A trocar is then used to puncture the body cavity. The piercing tip or obturator of the trocar is inserted through the cannula or sheath and the cannula partially enters the body cavity through the incision made by the trocar. The obturator can then be removed from the cannula and an elongated endoscope or camera may be inserted through the cannula to view the body cavity, or surgical instruments may be inserted to perform ligations or other procedures.

A great deal of force is often required to cause the obturator to pierce the wall of the body cavity. When the piercing tip breaks through the cavity wall, resistance to penetration ceases and the tip may reach internal organs or blood vessels, with resultant lacerations and potentially serious injury. The creation of the pneumoperitoneum provides some free space within which the surgeon may stop the penetration of the trocar. To provide further protection, trocars have more recently been developed with spring loaded shields surrounding the piercing tip of the obturator. Once the piercing tip of the obturator has completely pierced the body cavity wall, the resistance of the tissue to the spring loaded shield is reduced and the shield springs forward into the body cavity and covers the piercing tip. The shield thereby protects internal body organs and blood vessels from incidental contact with the piercing tip and resultant injury. Trocars including various safety shield designs are described in Yoon, U.S. Pat. No. 4,535,773; Moll, U.S. Pat. No. 4,654,030; and Moll, U.S. Pat. No. 4,601,710. An improved piercing tip comprised of a pointed blade with an improved safety shield is also the subject of commonly owned pending U.S. Ser. No. 08/038,904.

Once the cannula has been introduced into the opening in the body cavity wall, the pneumoperitoneum may be maintained by introducing gas into the abdominal cavity through the cannula. Various seals and valves have been utilized to allow abdominal pressure to be maintained in this fashion. Maintaining abdominal pressure is important both to allow working room in the body cavity for instruments introduced through the cannula, and to provide free space for the puncturing of the body cavity wall by one or more additional trocars as may be required for some procedures.

While the existing trocars and cannulas have proven useful, several disadvantages remain. The force required to cause the piercing tip to penetrate a body cavity wall is often so great that some physicians must strain to use the trocar with resulting loss of control over the depth of penetration of the instrument. In addition, the existing shield mechanisms do not spring forward to cover the obturator tip as quickly as possible. The delay in covering the piercing tip exposes the patient to unnecessary risk of internal laceration.

Also, with the current emphasis on cost controls in health care, it is desirable to utilize reusable medical instruments whenever possible. The difficulties of cleansing, disinfecting and otherwise decontaminating used trocars has made this a time consuming or impossible task, especially for shielded trocars. Therefore, a need exists for an improved apparatus for performing laparoscopic and similar surgical procedures.

SUMMARY OF THE INVENTION

Accordingly, it is the primary object of the invention to provide a safer trocar for piercing body cavity walls.

It is also an object of the invention to provide an improved shield design which will provide faster coverage of the obturator's piercing tip.

It is a further object of the invention to provide improved coatings for shields and cannulas which will permit easier penetration of body cavity walls and faster coverage of the obturator's piercing tip.

It is another object of the invention to provide a cannula which may be substantially reused without the need for excessive labor in cleaning and decontamination.

It is still another object of the invention to provide a seal or valve which permits easy insertion of surgical and exploratory instruments through the cannula yet still operates effectively to maintain the pneumoperitoneum in the body cavity.

Accordingly, the present invention provides a cannula with a detachable cap and disposable seal assembly and stopcock. To achieve faster shield protection, the forward or distal end of the shield is bottleshaped and is biased to move forward to cover the obturator's piercing tip when the piercing tip penetrates the body cavity wall. The shield may also be fabricated from or treated with hydrophilic materials so that when it is dipped in sterile water or other wetting solution before use, there is less friction between the shield and the body cavity wall allowing faster coverage of the piercing tip. To achieve easier penetration of body cavity walls by the cannula, the cannula may also be treated with a hydrophilic coating. A novel and inexpensive flexible valve is also provided which facilitates insertion of surgical instruments.

BRIEF DESCRIPTIONS OF THE DRAWINGS

FIG. 7A illustrates a side view of the improved shield design in its fully extended position covering the pointed blade of the obturator.

FIG. 7B illustrates a top view of the shield of FIG. 7A.

FIG. 8A illustrates a side view of the improved shield design in a partially retracted position exposing only portions of the sharpened edges of the pointed blade of the obturator, but covering the sharp tip of the blade.

FIG. 8B illustrates a top view of the shield of FIG. 8A.

FIG. 9A illustrates a side view of the improved shield design in a fully retracted position exposing the tip and sharpened edges of the pointed blade of the obturator.

FIG. 9B illustrates a top view of the shield of FIG. 9A.

DESCRIPTION OF THE PREFERRED EMBODIMENTS

Figure 1A:
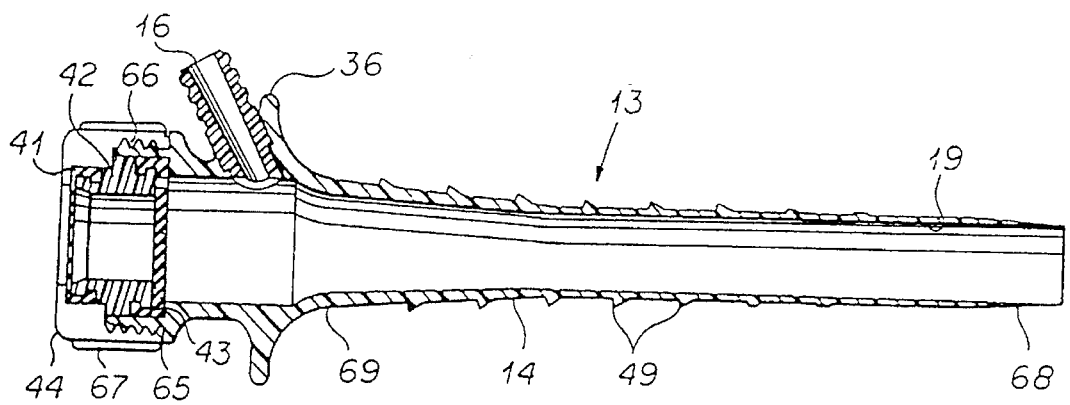
FIG. 1A is a cross sectional side view of an improved cannula according to the invention with a disposable gland retainer and end cap.
Figure 1B:
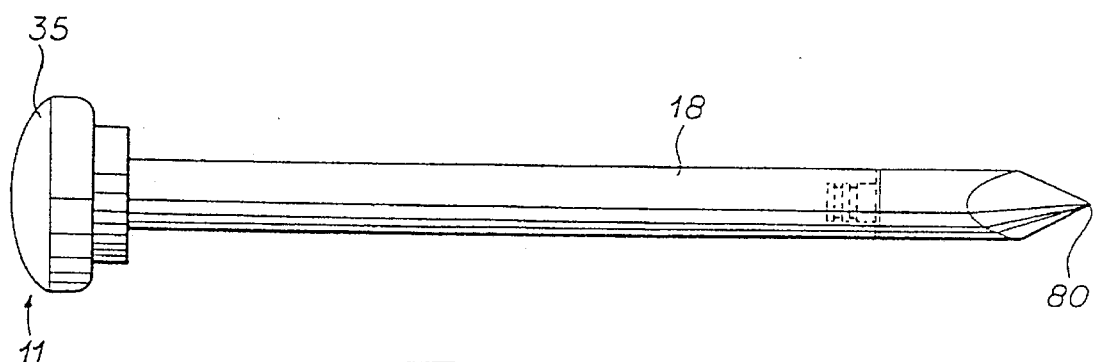
FIG. 1B is a side view of a conventional obturator which is adapted for use with the cannula of FIG. 1A.

The invention commonly known as a trocar is comprised of two major components. These are a cannula 13 such as those illustrated in FIGS. 1A and 6B, and an obturator such as the traditional obturator 11 in FIG. 1B or the shielded obturator 12 illustrated in FIG. 6A. The obturator 11 of FIG. 1B and cannula 13 of FIG. 1A are interfitting and as explained below are used together to penetrate a body cavity wall. Once the body cavity wall is penetrated, however, the obturator 11 may be removed and other medical instruments may be introduced into a lumen 19 of the cannula 13.

Figure 3A:
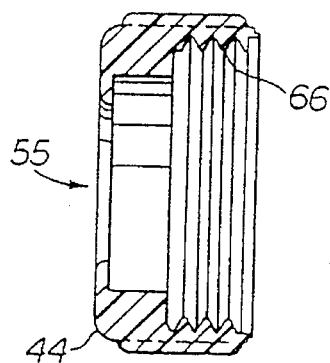
FIG. 3A is a cross sectional side view of the end cap of the improved cannula of FIG. 1 in isolation.
Figure 3B:
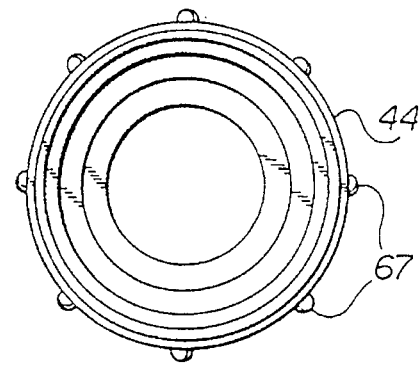
FIG. 3B is an end view of the end cap of the improved cannula of FIG. 1.

The cannula 13 of FIG. 1A consists of three components and two seal assemblies. The components are the cannula tube 14, the gland retainer 42 and the cap 44. The outer surface of the cannula tube 14 of FIG. 1A is shown with a helically wound thread 49 preferably beginning at a reduced height a short distance from the distal end 68 of the cannula tube 14 and gradually increasing to its full height as it proceeds toward the proximate end 69. At the proximate end 69 of the cannula tube 14, there is a raised flange 36 for convenience in handling the cannula 13. The proximal end of the cannula above the raised flange 36 forms a handle. Above the flange 36 is a gas port 16 which can be connected to a gas supply, not shown, to supply gas through the lumen 19 of the cannula tube 14 into a body cavity to create or maintain pneumoperitoneum. Above the gas port 16 are male threads 65 which allow the cannula tube 14 to be securely coupled with cap 44 which has corresponding female threads 66. The cap 44 also has an aperture 55 to permit insertion of an obturator 11, and gripping protrusions 67 to facilitate fastening and unfastening the cap 44. Mounted concentrically mostly within the proximate end 69 of the cannula tube 14 and held in place by the cap 44 is the gland retainer 42. The cap 44 is shown in isolation in FIGS. 3A and 3B.

Figure 2:
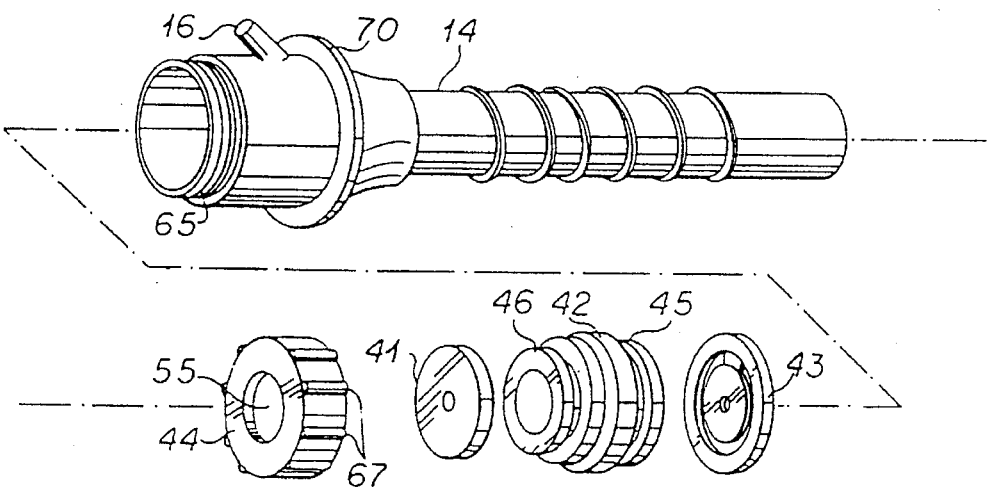
FIG. 2 is an exploded perspective view of the improved cannula of FIG. 1.
Figure 4A:
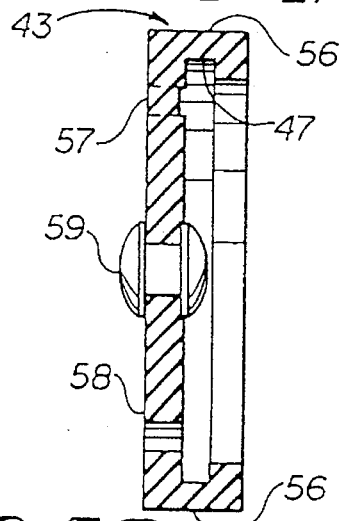
FIG. 4A is a cross sectional side view of the flexible flapper valve of the improved cannula of FIG. 1 in isolation.
Figure 4B:
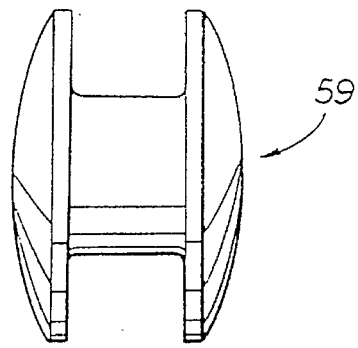
FIG. 4B is an enlarged side plan view of the button which is mounted in the center of the preferred embodiment of the flexible flapper valve.
Figure 5:
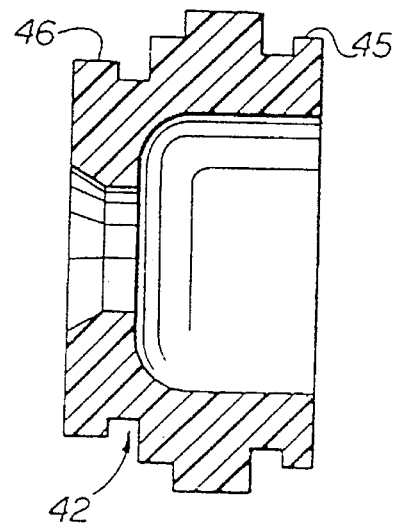
FIG. 5 is a cross sectional side view of the gland retainer of the improved cannula of FIG. 1 shown in isolation.

The gland retainer 42 shown in isolation in FIG. 5, holds two seals, 43 and 41, in place. A raised edge 45 at the distal end of the gland retainer 42 fits within a channel 47 shown in FIG. 4A formed by the C shaped edge 56 of flexible flapper seal 43, shown in FIGS. 1A and 2. A second raised edge 46 at the proximate end of the gland retainer 42 fits with a channel formed by the C shaped edge of wiper seal 41. Both the membrane seal 41 and flexible flapper seal 43 are fabricated from materials having sufficient elasticity that the edges of the seals 41 and 43 can be stretched over ridges 46 and 45 respectively.

Figure 4C:
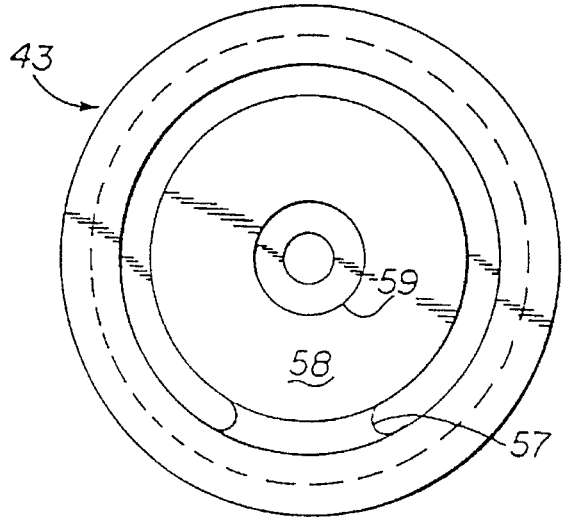
FIG. 4C is an end view of the flexible flapper valve of the improved cannula of FIG. 1.

The wiper seal 41 is of conventional design, however, the flexible flapper valve 43 is of novel construction. As shown in FIGS. 4A and 4C, a hinge 57 extends inward from the edge 56 of the flexible flapper valve 43 and mounted on the hinge is the flapper 58. In the preferred embodiment a hard plastic or metal button 59 is mounted on or through the flapper. When the piercing tip 80, shown in FIG. 1A, of an obturator 11 is inserted through the opening 55 in the cap 44, and through the wiper seal 41, the piercing tip contacts the hard button 59 of the flexible flapper valve 43 and begins to deflect the flapper 58 from its normal closed position flush against the distal end of the gland retainer 42. Because the flapper 58 is preferably molded or stamped in one piece with the hinge 57 and edge 56 of an elastomeric material, the piercing tip of the obturator might otherwise penetrate or cut into the flapper 58 which could cause resistance to entry of the obturator or damage the flapper 58 so that it would no longer seal the cannula 13 or gland retainer 42 effectively against loss of air through the opening 55 in the cap 44. The hard button 59 alleviates these possible problems.

When the obturator 12 or other endoscopic instrument is removed from the cannula 13, the resiliency of the hinge 57 causes the flapper 58 to move to a partially closed position. The flapper 58 is then firmly closed and sealed by action of the air pressure from the inflated body cavity, such air pressure pushing the flapper 58 against the edges of the distal end of the gland retainer 42 and thereby forming an effective seal against further loss of gas.

In its preferred embodiment, the cannula tube 14 portion is manufactured of a durable material such as stainless steel or titanium alloys, capable of withstanding repeated high temperature cleaning and sterilization, while the gland retainer 42 is made of an inexpensive plastic. The cap 44 may be made of either type of material. The gland retainer 42, containing the flapper valve and possibly also containing a wiper seal, is difficult to clean and sterilize. However, the gland retainer 42 and seals 41 and 43 are relatively inexpensive to manufacture and can be discarded after each use. The cannula tube 14, and optionally the cap 44, are relatively easy to clean and sterilize and need not be discarded. By reusing the cannula tube 14, and the cap 44 if manufactured of an appropriate material, cost and waste can be minimized. If desired the cap 44 can also be manufactured of inexpensive plastic and discarded with the gland retainer 42 after use.

Figure 6A:
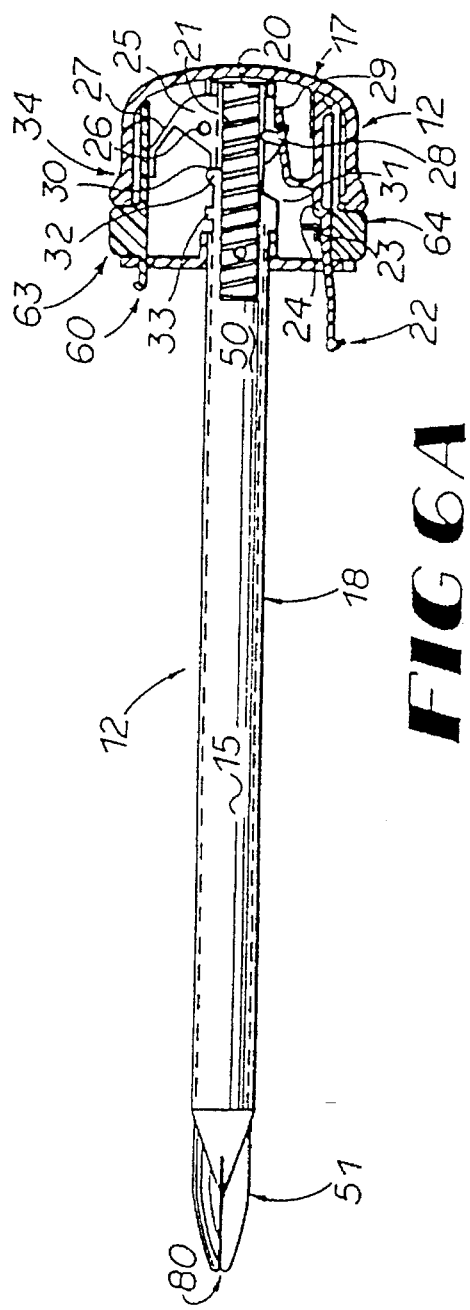
FIG. 6A is a side view in partial cross section of an obturator with an improved shield design and mechanism according to the present invention.

A shielded obturator 12 is shown in greater detail in FIG. 6A. The shielded obturator 12 in FIG. 6A includes an obturator housing 17 which forms a grip or handle. The shielded obturator 12 also includes a hollow obturator sheath 18, the proximal end of which is mounted to the obturator housing 17. The distal end of the obturator sheath 18 is fitted with a piercing tip 80. Housed within the obturator sheath 18 is the shield 15, shown in its extended position with the distal end 51 covering the piercing tip 80. The proximal end 50 of the shield 15 is received some distance within the hollow obturator sheath 18 where it is outwardly biased by a biasing means such as the coiled spring 21 interposed between the proximal end 50 of the shield 15 and the inner wall 20 of the obturator housing 17.

Still referring to FIG. 6A, a double action latch 34 for locking the shield 15 in both the extended position and a partially retracted position is illustrated. The latch 34 comprises a biasing means such as the spring 27, a blocking member such as the illustrated pivoting chock 25, an actuator such as the trigger 48, shown in FIG. 6B, and a linkage between the actuator and the blocking member such as the linking member 24. The illustrated latch operates to keep the shield 15 locked in the extended position except when armed or actuated. To lock the shield 15, a solid portion 30 of the pivoting chock 25 engages with a first lug 32 on the proximal end 50 of the shield 15 to prevent the shield 15 from retracting further toward the inner wall 20 of the obturator housing 17 and thereby exposing the piercing tip 80.

Figure 6B:
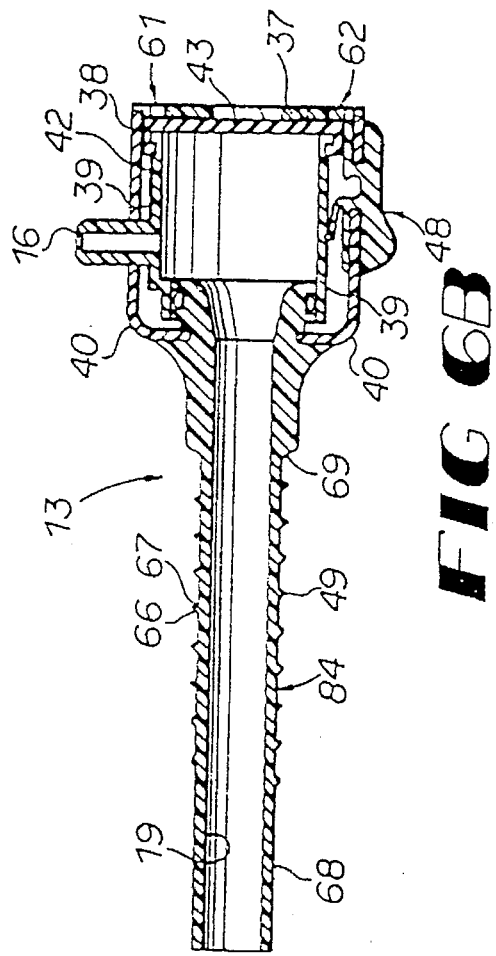
FIG. 6B is a cross sectional side view of a cannula with a flexible flapper valve for use with the obturator of FIG. 6A.

In order to permit the shield 15 to be retracted, the latch 34 must first be armed or actuated. To accomplish this, the shielded obturator 12 and cannula 13 must first be interfitted. In FIG. 6A and 6B, the distal end 22 of the linking member 24 from the shielded obturator 12 is received through opening 62 and engaged in the trigger 48 mounted in the cannula 13. Also a guiding tab 60 from the shielded obturator 12 is received in an opening 61 in the cannula 13. By depressing push buttons 63 and 64, the guiding tab 60 and linking member 24 can be disengaged, allowing for easy separation of the shielded obturator 12 from the cannula 13.

To arm the latch 34 in the embodiment illustrated in FIG. 6A, the distal end 22 of the linking member 24 engages with a trigger 48, shown in FIG. 6B. When the trigger 48 is depressed and pushed forward toward the piercing tip 80, the linking member 24 is likewise pulled forward. A hook 29 on the proximate end of the linking member 24 is engaged in a cradle 28 on the pivoting chock 25. As the linking member 24 is pulled forward, it causes the pivoting chock 25 to turn on its pivot 26 and thereby rotates the solid portion 30 away from the lug 32 on the proximal end 50 of the shield 15. This arms or actuates the obturator 12.

As the trigger 48 continues forward, the linking member 24 also travels forward until a stop block 23 halts further movement. When the stop block 23 halts further movement, the linking member 24 is in measured close proximity to a cam 31 protruding from the proximal end 50 of the shield 15. As soon as the surgeon applies pressure to the trocar 10, the proximal end 50 of shield 15 is pushed back into the housing 17. After the shield 15 is pushed back sufficiently that a second lug 33 on the proximal end 50 of the shield 15 has reached the solid portion 30, the cam 31 on the proximal end 50 of the shield 15 then dislodges the hook 29 of the linking member 24 from the cradle 28 of the pivoting chock 25. A biasing means such as the spring 27 acting on the pivoting chock 25 now causes the solid portion 30 of the pivoting chock 25 to try to return to its original locking position. When the shield 15 is fully retracted, the pivoting chock 25 cannot return to a locking position. Yet if the shield 15 should extend even partially, so that it is no longer fully retracted, the solid portion 30 of the pivoting chock 25 can engage the second lug 33, and become locked against the shield again becoming fully retracted. This is referred to as a partially locked or semi-protective position. In this fashion the second lug 33 acts as a detent allowing the shield to rachet forward to an extended position.

If the distal end 51 of the shield 15 and piercing tip 80 are properly designed, the partially locked position can provide substantial protection to the patient. With the pointed blade designs discussed in FIGS. 7–9, it is possible to have the shield cover the sharp tip 87 of the blade and allow only the sharpened edges 91 of the blade to remain exposed as shown in FIG. 8. This allows the sharpened edges 91 to continue cutting the body cavity wall but without risk of exposing the sharp tip 87 thus reducing the chance of inadvertent injury during the incision.

When the entire piercing tip 80 of the obturator 18 has passed through the body cavity wall and there is no resistance to the spring loaded shield 15, the shield 15 will spring completely forward to cover the piercing tip 80, as shown in FIGS. 6A and 7, and the pivoting chock 25 will pivot into its original locking position, where the solid portion 30 of the pivoting chock 25 acts to block rearward movement of the first lug 32 on the proximate end 50 of the shield 15. In this fashion, once the body cavity wall has been pierced by the sharp tip 87 and the shield 15 has partially locked, the shield 15 cannot again retract to expose the sharp tip 87 of the piercing tip 80 unless the operating physician uses the trigger 48 to rearm the trocar 10. Once the piercing tip 80 has completely penetrated the body cavity wall and the shield 15 has fully locked, the shield 15 it cannot again retract to oppose any portion of the piercing tip 80.

Referring again to FIG. 6B, the cannula 13 includes an outer housing 40, an inner housing 39, and a cannula tube 84 which is secured to and extends from the inner housing 39. In addition, the inner housing 39 is mounted within the outer housing 40. The inner housing 39 contains a gas sealing means such as the illustrated flexible flapper valve 43. The flexible flapper valve 43 will allow the introduction of the obturator sheath 18 of a shielded obturator 12, or other endoscopic instruments (not illustrated) without substantial loss of gas from the body cavity. As shown in FIG. 6B, when no instrument is inserted, the flapper 43 closes against the end plate 37 to maintain the gaseous pressure in the body cavity.

FIGS. 7–9 illustrate the presently preferred embodiment of the piercing tip 80, which is comprised of a pointed blade 81. The illustrated pointed blade 81 is substantially planar and has a central sharp tip or pointed distal end 87 and straight sharpened edges 91 proceeding from both sides of said distal end 87 to the shoulders 88. In alternative constructions, the blade 81 may have slight convex or concave curve to the sharpened edges 91. The point of the blade may be acute as illustrated or rounded. Other variations of a pointed blade or blades may also be utilized.

As shown in FIG. 7A and 7B, the distal end 51 of the shield 15 used with the illustrated pointed blade is "bottle shaped" or "dolphin nose shaped" in that it has a blunt end 92 at its most distal point which widens slowly at first and then more rapidly so that there is a slight concavity 94 as the distal end 51 of the shield 15 proceeds from the blunt end 92 to a shoulder 93. As shown in FIGS. 8A and 8B, when the shield end 51 is of this shape, it is possible for the blunt end 92 to cover the pointed distal end 87 of the blade 81 so that no additional penetration is possible, while still leaving portions of the sharpened edges 91 exposed. In this fashion, when the pointed distal end 87 of the blade 81 has penetrated the body cavity wall, but before the blade 81 is entirely through the wall, the blunt end 92 of the shield can move forward and be partially locked while still allowing the sharpened edges 91 of the pointed blade 81 to expand the incision in the body cavity wall so that the obturator and cannula may be introduced to communiate with the body cavity.

Figure 10A:
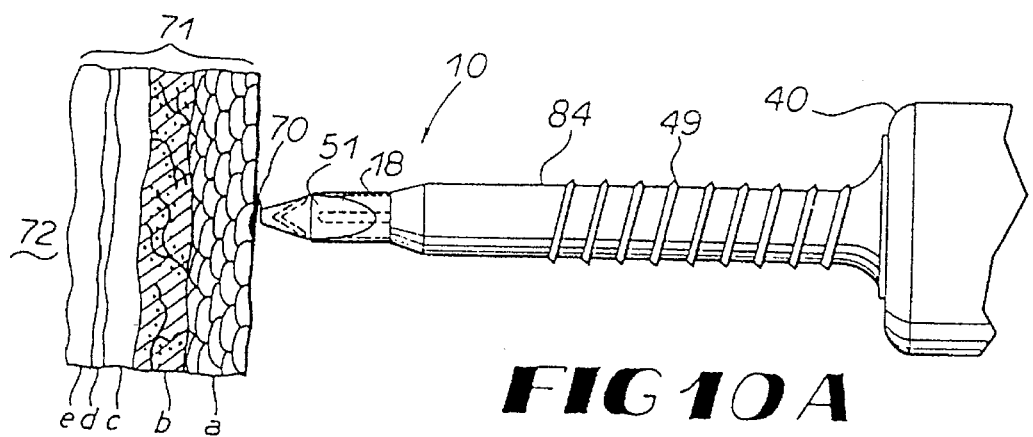
FIGS. 10A through 10D show, in sequential diagrammatic sectional views, an embodiment of the present invention as used to puncture a body cavity wall of a patient.
Figure 10B:
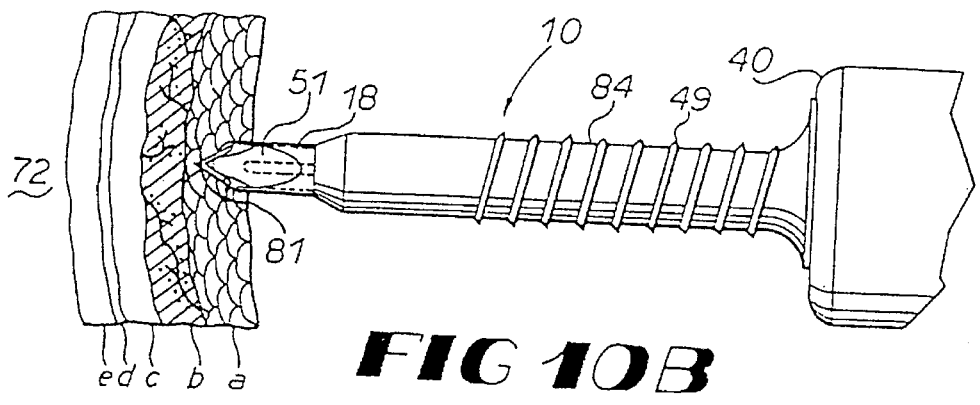

FIGS. 10A through 10D illustrate the piercing tip 80 and shield end 51 of the trocar 10 formed from the obturator 12 and cannula 13 of FIGS. 6A and 6B in use. In FIG. 10A, a small incision 70 is made in the surface of the skin or epidermis "a" of the body cavity wall 71 of a patient. The piercing tip 80, in this case the pointed blade 81, of the trocar 10 with extended shield 51 may then be placed against the incision 70 as shown. When the trocar 10 is in this position, it may be armed or actuated by depressing the trigger 48 (shown in FIGS. 6A and 6B) and sliding the trigger 48 forward as explained above. When manual force is applied to the obturator housing 17 which forms the trocar handle (shown in FIG. 6A) pushing the trocar to the left, the resistance of the body cavity wall 71 holds back the distal end 51 of the shield 15 and the pointed blade 81 is exposed as shown in FIG. 10B. The pointed blade 81 then slices through the dermis "a" and subcutaneous tissue including fat cells, muscle, and facia, depicted as "b," "c," "d" and "e" in FIGS. 10A–10D. The various layers of the body cavity wall 71 vary depending upon the cavity being pierced, but in general, the layers of facia are particularly resistant to penetration.

Figure 10C:
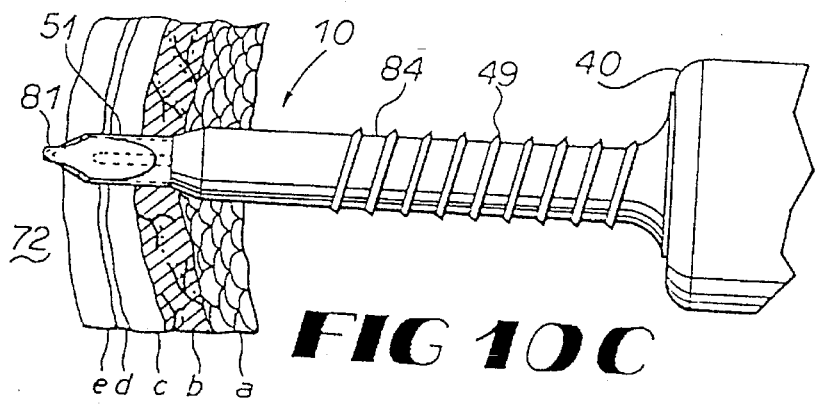

In FIG. 10C, immediately after the sharpened tip 87 of the pointed blade 81 has penetrated the innermost layer "e" of the body cavity wall 71, the blunt end 92 of the distal end 51 of the shield 15 is forced forward through the incision 70 by the bias of the coil spring 21. When the shield 15 reaches this partially retracted position and the preferred double action latch 34 of the obturator 12 illustrated in FIG. 6A is used, the shield 15 will lock so that it cannot be retracted to again expose the sharp tip 87 of the pointed blade 81, yet the shield 15 permits the sharp edges 91 of the blade 81 to continue cutting. This is a semi-protected shield position. In this partially locked or semi-protected position the interior of the body cavity 72 and organs, blood vessels and other anatomical structures are protected against puncture by the sharp end 87 of the blade 81.

Figure 10D:
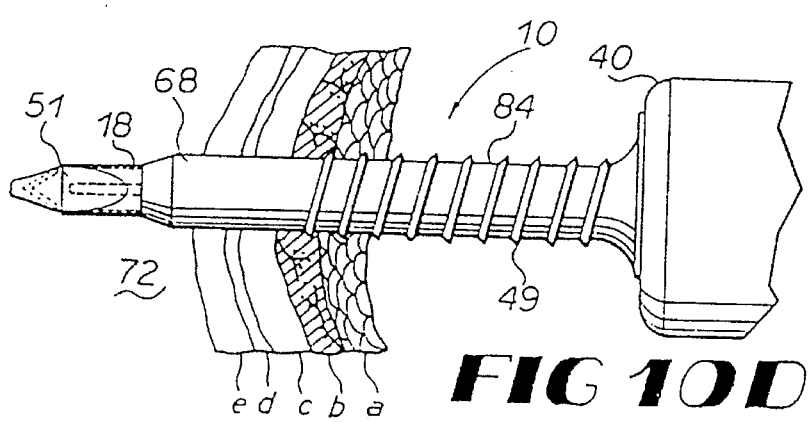

FIG. 10D shows that the shield end 51, the obturator sheath 18, and the distal end 68 of the cannula tube 84 all proceed through the incision 70 in the body cavity wall 71 as manual force continues to be applied to the trocar 10. Just as the shoulder 93 of the distal end 51 of the shield 15 passes through the inner layer "e" of the body cavity wall 71, the resistance of the body cavity wall 71 is significantly reduced and the shield 15 is pushed to its fully extended position with the distal end 51 covering the pointed blade 81. This action completely protects the interior of the body cavity 72 immediately after the full penetration of the pointed blade 81 through the body cavity wall 71 and protects organs, blood vessels and other anatomical structures from incidental contact even with the sharpened edges 91 of the blade 81. Simultaneously with the full extension of the shield 15 into its protective position covering the pointed blade 81, the pivoting chock 25 engages the first lug 32 on the proximate end 50 of the shield 15, which prevents the shield 15 from being retracted to expose the pointed blade 81 until the trocar 10 is again actuated by depressing and moving the trigger 48 forward.

In order to improve the performance of the shield 15 in moving forward through the body cavity wall, it is possible to either mold the shield 15 or shield end 51 from a hydrophilic plastic or to coat the shield with a hydrophilic coating. By providing the shield end 51 with appropriate hydrophilic properties, the shield end 51 can be dipped in a wetting solution, usually of water or an appropriate alcohol solution, and the shield end 51 will then have a lower coefficient of friction and will more easily slide through the incision 70 in the body cavity wall 71 to cover the piercing tip 80. Appropriate coatings or compounds must be substantially nonreactive with respect to living tissue and non-thrombogenic when in contact with blood. Appropriate hydrophilic coatings would include polyvinylpyrrolidone-polyurethane or polyvinybutyrol interpolymers as described in U.S. Pat. Nos. 4,100,309 and 4,119,094. Appropriate molding compounds, which could alternatively also be applied as coatings, include hydrophilic polymer blends with thermoplastic polyurethane or polyvinylbutyrol and hydrophilic polyvinylpyrrolidone or other poly(N-vinyl lactans) as described in U.S. Pat. Nos. 4,642,267 and 4,847,324. An appropriate hydrophillic coating will reduce the coefficient of friction for stainless steel by over 60% and can reduce the coefficients of friction for plastics by over 90%. This permits hydrophillic plastics to be used for the shield 50 rather than steel.

The same hydrophilic coatings or compounds may also be used in the cannula 13 which will facilitate the entry of the distal end 68 of the cannula 13 into the incision made by the obturator 12. Although the sharpened blade 81 does not provide substantial resistance, some minor improvement might also be achieved by applying a hydrophillic coating to this blade 81.

Numerous alterations of the structures herein described will suggest themselves to those skilled in the art. It will be understood that the details and arrangements of the parts that have been described and illustrated in order to explain the nature of the invention are not to be construed as any limitation of the invention. All such alterations which do not depart from the spirit of the invention are intended to be included within the scope of the appended claims.

We claim:

1. A shielded obturator comprising:

(a) an obturator sheath having a distal end and a proximate end;

(b) a handle mounted to the proximate end of said obturator sheath;

(c) a pointed blade on the distal end of the obturator sheath said pointed blade having a sharpened point at a distal end and sharpened lateral portions;

(d) a shield slidably mounted to the obturator sheath and movable relative to the pointed blade between an extended protective position, a partially retracted semi-protective position covering the sharpened point of the pointed blade while leaving at least a portion of the sharpened lateral portions exposed for cutting tissue, and a retracted unprotected position; and (e) a biasing means tending to bias the shield into the extended protective position.

2. The shielded obturator of claim 1 further comprising a latch means engaging with said shield and permitting the shield to be locked in both the extended protective position, and the partially retracted semi-protective position.

3. The shielded obturator of claim 2 wherein the latch means is actuatable to allow the shield to slide from its extended protective position towards its retracted unprotected position when force is applied to said shield.

4. The shielded obturator of claim 3 wherein said shield has a distal end to cover the pointed blade and a proximate end, and said latch means is comprised of a blocking member, and a plurality of longitudinally spaced detents on the proximate end of the shield which said blocking member may engage to prevent the shield from retracting.

5. The shielded obturator of claim 1 wherein said shield has a distal end to cover the pointed blade and a proximate end, and said distal end is provided with a hydrophillic coating.

6. The shielded obturator of claim 1 wherein the pointed blade is substantially planar, wherein said sharpened lateral portions comprise a first sharpened edge proceeding from the sharpened point to a first shoulder, and a second sharpened edge proceeding opposite the first sharpened edge to a second shoulder.

7. The shielded obturator of claim 6 wherein the shield is of cylindrical shape and is slidable mounted within the obturator sheath, said shield having a proximal end received within the obturator handle, and a distal end having a channel of sufficient depth and width to receive the pointed blade within said distal end of the shield.

8. The shielded obturator of claim 7 in which the distal end of the shield has a blunt end and proceeds along a concave curve to a shoulder portion, said shoulder portion being of substantially the same width as an interior of the obturator sheath.

9. The shielded obturator of claim 8 wherein the blunt end of the shield covers the sharpened point when said shield is positioned in the partially retracted semi-protective position, yet the concave curve of the distal end of the shield permits the first and second sharpened edges of the pointed blade adjacent to the shoulders of the pointed blade to remain exposed.

10. The shielded obturator of claim 7 wherein the distal end of the shield is provided with a hydrophillic coating.

11. A trocar comprising:
   (a) a cannula with a housing and a cannula tube, the canula tube having a lumen of sufficient diameter to receive an obturator sheath;
   (b) a shielded obturator having a handle, an obturator sheath interfitting in the lumen of the cannula tube and having a proximal end joined to said handle and also having a distal end to which a pointed blade is mounted the pointed blade including a sharpened point and sharpened lateral portions;
   (c) a shield slidably mounted interiorly of the obturator sheath and moveable relative to the pointed blade between an extended protective position, a partially extended semi-protective position, and a retracted unprotected position covering the point while leaving at least a portion of the sharpened lateral portions exposed for cutting tissue; and
   (d) a biasing means tending to bias the shield into the extended protective position.

12. The trocar of claim 11 further comprising a latch means engaging with said shield and permitting the shield to be locked in the extended protective position and the partially extended semi-protective position.

13. The trocar of claim 11 in which the pointed blade is substantially planar; said sharpened lateral portions comprising a first sharpened edge proceeding from the point to a shoulder, and a second sharpened edge proceeding opposite the first sharpened edge to a second shoulder.

14. The trocar of claim 13 wherein said shield has a distal shield end to cover the pointed blade and a proximate shield end, and the latch means is comprised of a blocking member, and a plurality of longitudinally spaced detents on the proximate shield end which said blocking member may engage to prevent the shield from retracting.

15. The trocar of claim 13 in which the shield is of generally cylindrical shape, said shield having a proximal end received within the obturator handle, and a blunt distal end having a channel of sufficient depth and width to receive the pointed blade within the distal end of the shield.

16. The trocar of claim 15 in which the distal end of the shield proceeds along a concave curve to a shoulder portion, said shoulder portion being of substantially the same width as an interior of the obturator sheath.

17. The trocar of claim 16 wherein the blunt distal end of the shield covers the point when said shield is positioned in the partially retracted semi-protective position, yet the concave curve of the blunt distal end of the shield permits the first and second sharpened edges of the pointed blade adjacent to the shoulders of the pointed blade to remain exposed.

18. The trocar of claim 15 wherein the distal end of the shield is provided with a hydrophillic coating.

19. The trocar of claim 11 wherein said shield has a distal end to cover the pointed blade and a proximate end, and said distal end is provided with a hydrophillic coating.

20. A method of using a trocar to penetrate a body wall comprising the steps of:
   i) providing a trocar having:
      (a) a cannula with a housing and a cannula tube containing a lumen of sufficient diameter to receive an obturator sheath;
      (b) a shielded obturator having a handle, an obturator sheath interfitting with the lumen of the cannula tube, said obturator sheath having a proximate end connected to said handle and a distal end, and a pointed blade with a sharpened tip mounted in the distal end of the obturator sheath;
      (c) a shield slidably mounted adjacent to the obturator sheath and moveable relative to the pointed blade between an extended position covering the pointed blade, a partially retracted semi-protective position at least partially covering the pointed blade, and a retracted position;
      (d) a biasing means tending to bias the shield into said extended position;
      (e) a latch means having at least two locked positions in which the shield is locked in either the extended position or the partially retracted semi-protective position, and having an actuated position which permits the shield to be forced into its retracted position;
   ii) actuating said latch means;
   iii) urging said cannula tube and pointed blade against the body wall to be penetrated, whereby said shield is pushed into said retracted position by the body wall to expose said pointed blade to penetrate the body wall and said latch means is biased to automatically resume a locking position upon return of the shield to either said partially retracted semi-protective position or said extended protective position;
   iv) urging said cannula tube and pointed blade against the body wall until the sharpened tip penetrates the body wall and the shield locks in the partially retracted semi-protective position;
   v) urging said cannula tube and pointed blade against the body wall until the pointed blade has completely penetrated the body wall and the shield locks in the extended protective position;
   vi) urging said cannula tube against the body wall until the lumen of the cannula tube communicates through the body wall.

* * * * *